US00PP16451P2

(12) United States Plant Patent
Verduin

(10) Patent No.: US PP16,451 P2
(45) Date of Patent: Apr. 18, 2006

(54) ***ASTILBE* PLANT NAMED 'HEART AND SOUL'**

(50) Latin Name: *Astilbe chinensis*
Varietal Denomination: Heart and Soul

(75) Inventor: Henricus Gijsbertus Johannes Verduin, Heemskerk (NL)

(73) Assignee: Witteman & Co., Hillegom (NL)

( * ) Notice: Subject to any disclaimer, the term of this patent is extended or adjusted under 35 U.S.C. 154(b) by 77 days.

(21) Appl. No.: 11/073,461

(22) Filed: Mar. 5, 2005

(51) Int. Cl.
*A01H 5/00* (2006.01)

(52) U.S. Cl. ..... Plt./263

(58) Field of Classification Search ..... Plt./263
See application file for complete search history.

(56) References Cited

U.S. PATENT DOCUMENTS

PP14,964 P2 * 6/2004 Verduin ..... Plt./263
PP14,969 P2 * 6/2004 Verduin ..... Plt./263

* cited by examiner

*Primary Examiner*—Kent Bell
*Assistant Examiner*—W. C. Haas
(74) *Attorney, Agent, or Firm*—C. A. Whealy

(57) ABSTRACT

A new and distinct cultivar of *Astilbe* plant named 'Heart and Soul', characterized by its upright, mounded and compact plant habit; rapid growth rate; freely and uniform flowering habit; and light purple-colored flowers.

2 Drawing Sheets

Botanical designation: *Astilbe chinensis.*
Cultivar denomination: 'Heart and Soul'.

BACKGROUND OF THE INVENTION

*The present Invention relates to a new and distinct cultivar of Astilbe* plant, botanically known as *Astilbe chinensis*, and hereinafter referred to by the name 'Heart and Soul'.

The new *Astilbe* orignated from a chance pollination of two unknown *Astilbe chinensis* selections. The new *Astilbe* was discovered and selected by the Inventor as a single flowering plant originating from a group of open-pollinated crosses made in a controlled environment in Heemskerk, The Netherlands in 1999. The new *Astilbe* was selected on the basis of its unique flower coloration.

Asexual reproduction of the new cultivar by divisions since 2000 in Heemskerk, The Netherlands, has shown that the unique features of this new *Astilbe* are stable and reproduced true to type in successive generations.

SUMMARY OF THE INVENTION

Plants of the cultivar Heart and Soul have not been observed under all possible environmental conditions. The phenotype may vary somewhat with variations in environment such as temperature and light intensity without, however, any variance in genotype.

The following traits have been repeatedly observed and are determined to be the unique characteristics of 'Heart and Soul'. These characteristics in combination distinguish 'Heart and Soul' as a new and distinct *Astilbe* cultivar:

1. Upright, mounded and compact plant habit.
2. Rapid growth rate.
3. Freely and uniformly flowering habit.
4. Light purple-colored flowers.

Plants of the new *Astilbe* can be compared to the *Astilbe* cultivar Gloria, not patented. In side-by-side comparisons conducted in Heemskerk, The Netherlands, plants of the new *Astilbe* differed from plants of the cultivar Gloria in the following characteristics:

1. Plants of the new *Astilbe* have darker green-colored leaves than plants of the cultivar Gloria.
2. Plants of the new *Astilbe* have larger inforescences and larger flowers than plants of the cultivar Gloria.

Plants of the new *Astilbe* can also be compared to the *Astilbe* cultivar Hyacinth, not patented. In side-by-side comparisons conducted in Heemskerk, The Netherlands, plants of the new *Astilbe* differed from plants of the cultivar Hyacinth in the following characteristics:

1. Plants of the new *Astilbe* have darker green-colored leaves than plants of the cultivar Hyacinth.
2. Plants of the new *Astilbe* have larger inflorescences and larger flowers than plants of the cultivar Hyacinth.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Astilbe.*

The photograph on the first sheet comprises a side perspective view of a typical flowering plant of 'Heart and Soul' grown in a container.

The photograph at the top of the second sheet is a close-up view of a typical inflorescence of 'Heart and Soul'.

The photograph at the bottom of the second sheet is a close-up view of typical leaves of 'Heart and Soul'.

DETAILED BOTANICAL DESCRIPTION

Plants shown in the aforementioned photographs and used in the following description were grown in containers under conditions which closely approximate commercial production conditions during the summer in an outdoor nursery in Hillegom, The Netherlands. Plants in the photographs and those used for the description were about one year old when the photographs and desciption were taken. During the production of the plants, day temperatures ranged from 14° C. to 30° C. and night temperatures ranged from 6° C. to 17° C. In the following description, color references are made to The Royal Horticultural Society Colour Chart, 2001 Edition, except where general terms of ordinary dictionary significance are used.

Botanical classification: *Astilbe chinensis* cultivar Heart and Soul.

Parentage:

*Female, or seed, parent.*—Unknown selection of *Astilbe chinensis.*

*Male, or pollen, parent.*—Unknown selection of *Astilbe chinensis.*

Propagation:

*Type.*—By divisions.

*Time to initate rooting.*—About two weeks at 14° C.

*Time to produce a rooted young plant.*—About 40 days at 20° C.

*Root description.*—Fine; white in color.

*Rooting habit.*—Freely branching; reasonably dense.

Plant description:

*Form.*—Perennial. Upright, mounded and compact plant habit; inverted triangle. Flowering stems and leaves arise from the roots; dense and bushy plant habit; moderately vigorous growth habit. Freely flowering with numerous flowers on numerous branched panicles.

*Growth rate.*—Rapid; from divisions, about 20 weeks are required to produce fully-grown flowering plants.

*Plant height.*—About 52 cm.

*Plant width.*—About 44 cm.

*Stem description.*—Length: About 24 cm. Diameter: About 5 mm. Internode length: About 12 cm. Strength: Strong. Texture: Sparsely pubescent. Color: 144A with random spots, N167B.

*Foliage description.*—Arrangement: Alternate; bi-ternately compound. Leaf length (excluding petiole): About 15.9 cm. Leaf width: About 20.3 cm. Lateral leaflet length: About 6 cm. Lateral leaflet width: About 3.7 cm. Terminal leaflet length: About 8 cm. Terminal leaflet width: About 5.2 cm. Lateral leaflet shape: Ovate. Terminal leaflet shape: Obovate. Lateral and terminal leaflet apex: Acute. Lateral and terminal leaflet base: Attenuate. Lateral and terminal leaflet margin: Biserrate. Lateral and terminal leaflet texture, upper and lower surfaces: Sparsely pubescent; rough. Lateral and terminal leaflet venation pattern: Pinnate. Lateral and terminal leaflet color: Developing foliage, upper and lower surfaces: 143A. Fully expanded foliage, upper surface: Darker than 137A; venation, 174A. Fully expanded foliage, lower surface: 137C; venation, 164A, towards the base N199C. Leaf petiole length: About 14.6 cm. Leaflet petiole length: About 2.3 cm. Leaf and leaflet petiole diameter: About 2 mm. Leaf and leaflet petiole texture, upper and lower surfaces: Smooth, glabrous. Leaf petiole color, upper and lower surfaces: 144A. Leaflet petiole color, upper surface: 175A. Leaflet petiole color, lower surface: 144A to 144B.

Flower description:

*Flower arrangement and shape.*—Numerous rotate single flowers arranged in branched panicles; flowers face upright, outward or droop. Freely and uniformly flowering habit; about 3,000 flowers and flower buds per plant; typically two panicles develop per plant.

*Natural flowering season.*—Continuous flowering during the summer in The Netherlands.

*Flower longevity on the plant.*—Indivdual flowers last about ten days on the plant. Flowers persistent.

*Fragrance.*—Moderate; sweet.

*Flower buds.*—Length: About 1.9 mm. Diameter: About 2 mm. Shape: Roughly globular. Color: 145A; towards the apex, 77B.

*Inflorescence height.*—About 28.5 cm.

*Inflorescence diameter.*—About 17.2 cm.

*Flowers.*—Diameter: About 8 mm. Depth (height): About 4 mm.

*Petals.*—Quantity per flower: About six. Length: About 4 mm. Width: About 0.5 mm. Shape: Linear; twisted. Apex: Acute. Margin: Entire. Texture, upper and lower surfaces: Smooth, glabrous. Color: When opening, upper and lower surfaces: N80C. Fully opened, upper and lower surfaces: 76C; color becoming closer to N76D to lighter than N76D.

*Sepals.*—Quantity per flower: About six. Length: About 2.5 mm. Width: About 1 mm. Shape: Ovate. Apex: Acute. Base: Cuneate, fused. Margin: Entire. Texture, upper and lower surfaces: Smooth, glabrous. Color: Immature, upper and lower surfaces: 145C. Mature, upper and lower surfaces: N155B.

*Peduncles.*—Length: About 35 cm. Diameter: About 4 mm. Angle: Erect to about 5° from vertical. Strength: Strong. Color: 144B to 144C.

*Pedicels.*—Length: About 0.5 mm. Diameter: About 0.5 mm. Angle: About 45° from vertical. Strength: Moderately strong. Color: N155B.

*Reproductive organs.*—Stamens: Quantity per flower: About ten. Filament length: About 1.8 mm. Anther attachment: Basifixed. Anther shape: Oblong. Anther length: About 0.2 mm. Anther color: N155A. Pollen amount: Scarce. Pollen color: 158D. Pistils: Quantity per flower: One. Pistil length: About 1.5 mm. Stigma shape: Club-shaped. Stimga color: N155A. Style length: About 1.2 mm. Style color: N155A. Ovary color: 145D.

*Fruit/seed.*—Fruit and seed development have not been observed.

Disease/pest resistance: Plants of the new *Astilbe* have not been noted to be resistant to pathogens and pests common to *Astilbe.*

High temperature tolerance: Plants of the new *Astilbe* have been observed to tolerate temperatures of 30° C.

Hardiness: Plants of the new *Astilbe* are hardy to USDA Zone 5.

It is claimed:

1. A new and distinct cultivar of *Astilbe* plant named 'Heart and Soul', as illustrated and described.

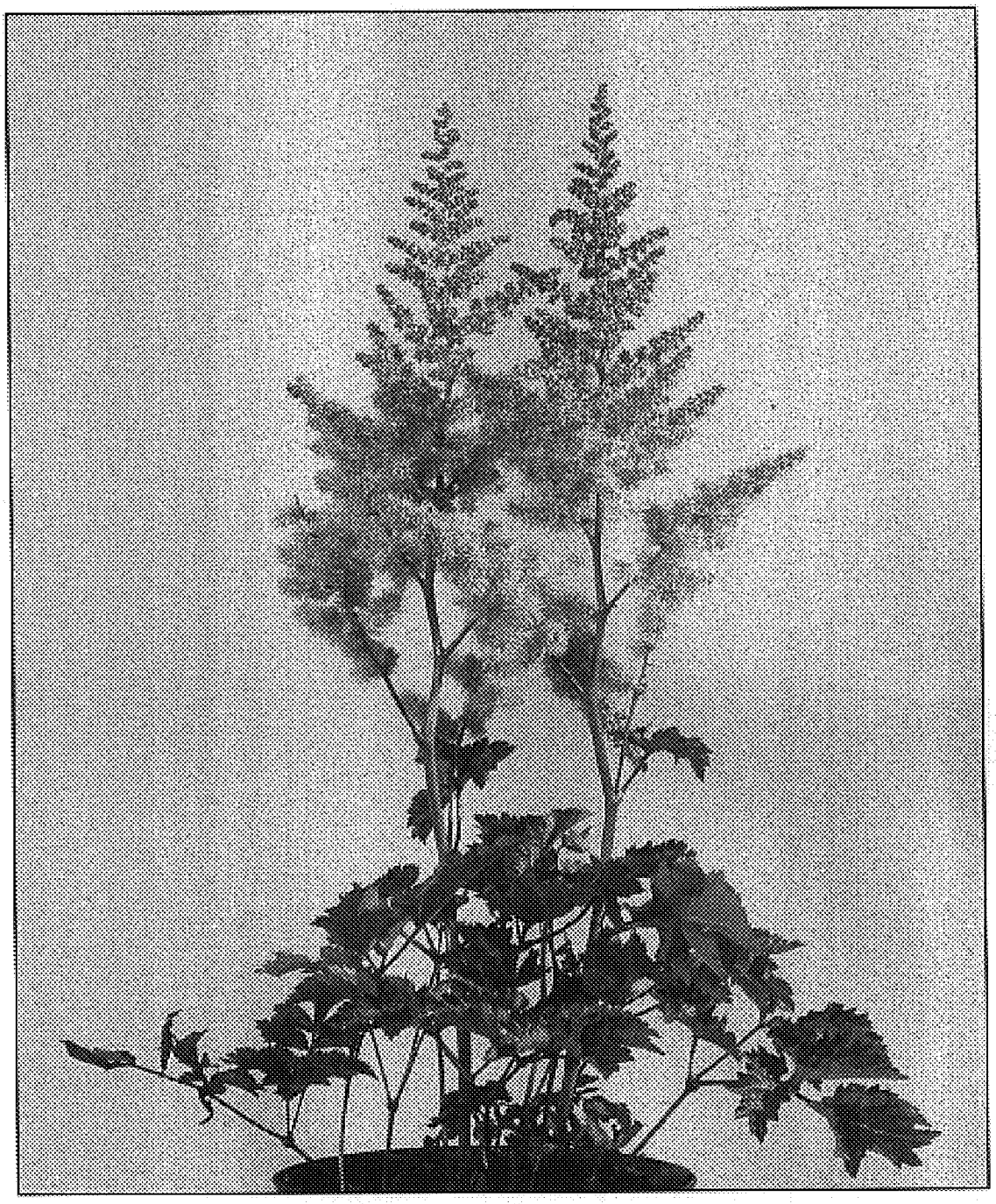

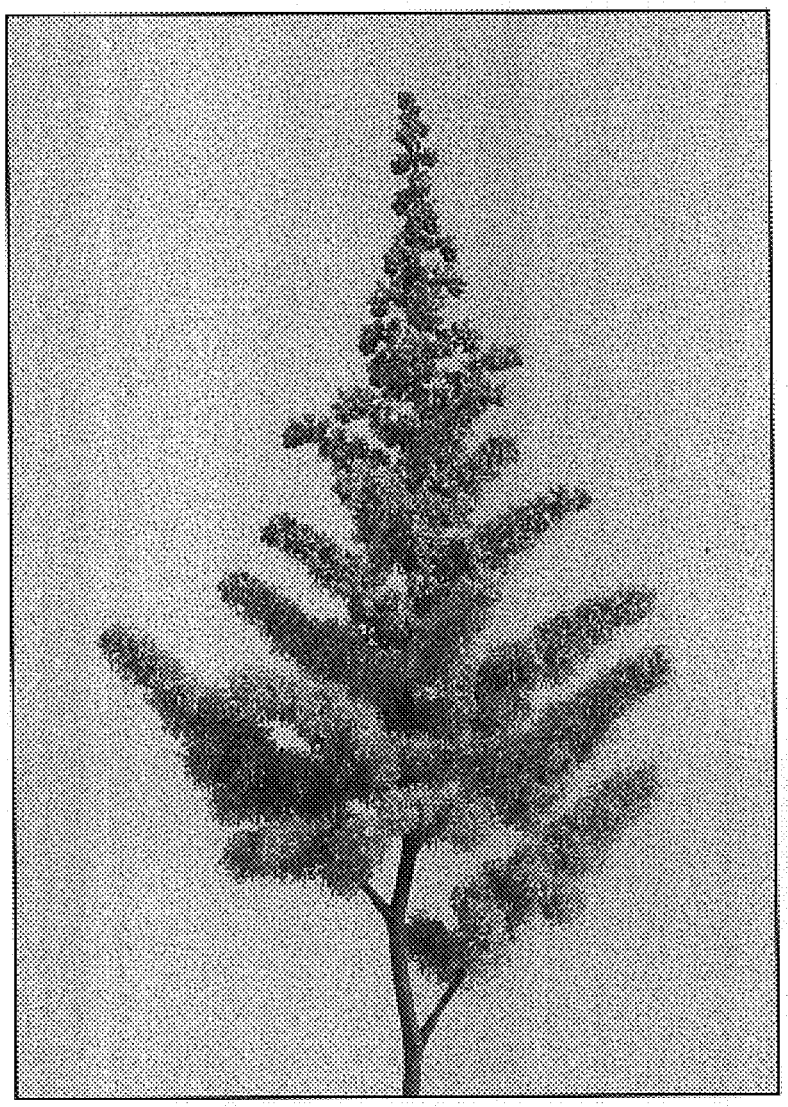
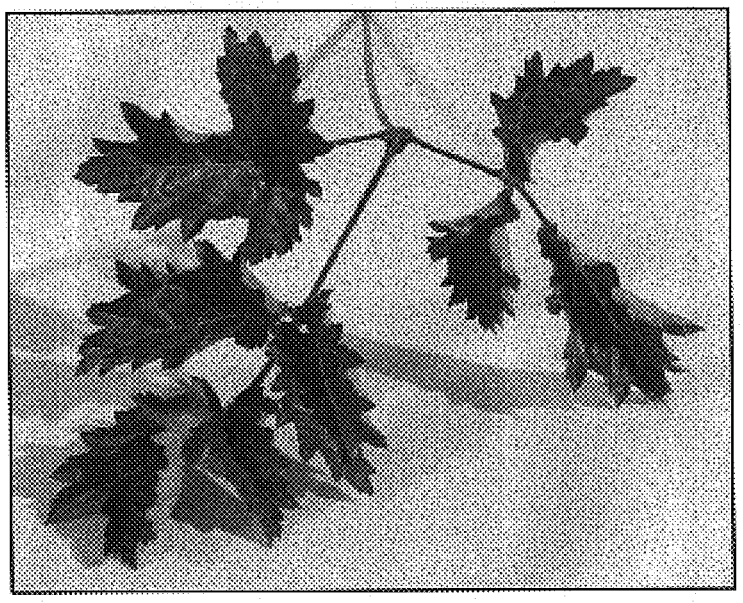

* * * * *